(12) United States Patent
Lucachick et al.

(10) Patent No.: US 10,345,168 B2
(45) Date of Patent: Jul. 9, 2019

(54) HIGH OUTPUT CHARPY SENSOR BODY

(71) Applicant: MTS Systems Corporation, Eden Prairie, MN (US)

(72) Inventors: Glenn Lucachick, Bloomington, MN (US); Richard A. Meyer, Chaska, MN (US); Robert Josephson, Sturgeon Bay, WI (US)

(73) Assignee: MTS SYSTEMS CORPORATION, Eden Prairie, MN (US)

( * ) Notice: Subject to any disclaimer, the term of this patent is extended or adjusted under 35 U.S.C. 154(b) by 0 days.

(21) Appl. No.: 15/833,758

(22) Filed: Dec. 6, 2017

(65) Prior Publication Data

US 2018/0156681 A1 Jun. 7, 2018

Related U.S. Application Data

(60) Provisional application No. 62/431,227, filed on Dec. 7, 2016.

(51) Int. Cl.
| | |
|---|---|
| *G01L 5/00* | (2006.01) |
| *G01N 3/14* | (2006.01) |
| *G01N 3/34* | (2006.01) |
| *G01L 5/16* | (2006.01) |

(52) U.S. Cl.
CPC .............. *G01L 5/0052* (2013.01); *G01N 3/14* (2013.01); *G01N 3/34* (2013.01); *G01L 5/161* (2013.01); *G01L 5/165* (2013.01); *G01N 2203/0039* (2013.01); *G01N 2203/0098* (2013.01)

(58) Field of Classification Search
CPC ....... G01L 5/0052; G01L 5/161; G01L 5/165; G01N 3/14; G01N 3/34; G01N 2203/0039; G01N 2203/0098

USPC .......................................................... 73/768
See application file for complete search history.

(56) References Cited

U.S. PATENT DOCUMENTS

| | | | |
|---|---|---|---|
| 2,359,044 A | 9/1944 | MacBride | |
| 2,362,589 A | 11/1944 | Simmons, Jr. | |
| 3,209,585 A | 10/1965 | Wolstenholme et al. | |
| 3,498,117 A | 3/1970 | Dalrymple | |
| 3,557,603 A | 1/1971 | Carr | |
| 3,969,935 A * | 7/1976 | Shoberg ............... | G01L 1/2218 73/862.629 |
| 3,985,025 A * | 10/1976 | Ormond ............... | G01L 1/2231 177/255 |
| 4,065,962 A * | 1/1978 | Shoberg ............... | G01G 3/1404 177/229 |
| 4,153,125 A * | 5/1979 | Hutchinson .......... | G01G 3/1404 177/211 |

(Continued)

FOREIGN PATENT DOCUMENTS

JP 2000097829 A 4/2000

OTHER PUBLICATIONS

International Search Report and Written Opinion dated Apr. 6, 2018 for corresponding International Application No. PCT/US2017/064845, filed Dec. 6, 2017.

*Primary Examiner* — Max H Noori
(74) *Attorney, Agent, or Firm* — Steven M. Koehler; Westman, Champlin & Koehler, P.A.

(57) ABSTRACT

An impact sensor body for sensing Charpy impact force is disclosed. The sensor body includes a body of material with a plurality of apertures. The apertures are configured within the body of material to form a flexure member orthogonal to a direction of motion to strike an object.

19 Claims, 6 Drawing Sheets

(56) References Cited

U.S. PATENT DOCUMENTS

| | | | |
|---|---|---|---|
| 4,425,786 A | | 1/1984 | Sirkkola et al. |
| 4,546,838 A | * | 10/1985 | Ormond .................. G01G 21/12 |
| | | | 177/211 |
| 4,615,209 A | | 10/1986 | Change, Jr. |
| 4,993,506 A | * | 2/1991 | Angel .................. G01G 3/1402 |
| | | | 177/211 |
| 5,510,581 A | * | 4/1996 | Angel .................... G01G 3/141 |
| | | | 177/211 |
| 5,677,475 A | | 10/1997 | Miyoshi |
| 6,253,626 B1 | * | 7/2001 | Shoberg ................ G01L 1/2231 |
| | | | 73/775 |
| 6,990,845 B2 | | 1/2006 | Voon et al. |
| 7,077,016 B2 | * | 7/2006 | Miyake .............. G01G 19/4142 |
| | | | 73/862.627 |
| 7,131,340 B2 | | 11/2006 | Bohme et al. |
| 7,320,242 B2 | | 1/2008 | Hoo Fatt et al. |
| 7,367,236 B2 | | 5/2008 | Georgeson et al. |
| 7,726,173 B2 | | 6/2010 | Vergano et al. |
| 9,377,386 B2 | | 6/2016 | Ruth et al. |
| 2003/0111277 A1 | * | 6/2003 | Aumard ............... G01G 3/1412 |
| | | | 177/229 |
| 2005/0241408 A1 | | 11/2005 | Scoot |
| 2006/0070463 A1 | * | 4/2006 | Walker .................. G01L 1/2243 |
| | | | 73/862.627 |
| 2016/0003696 A1 | * | 1/2016 | Longman ................. B62M 3/00 |
| | | | 73/862.621 |

\* cited by examiner

HIGH OUTPUT CHARPY SENSOR BODY

CROSS-REFERENCE TO RELATED APPLICATION

The present application claims the benefit of and priority to U.S. provisional patent application Ser. No. 62/431,227, filed Dec. 7, 2016, the contents of which are hereby incorporated by reference in its entirety.

BACKGROUND

The present invention is in the technical field of impact test sensors. More particularly, the present invention is in the technical field of Charpy impact test sensors.

Traditional Charpy impact tests utilize strain gages that measure compressive strains and are configured in a half-bridge circuit, diminishing the potential sensor output. Further, the strain gages and associated wiring used in Charpy impact tests are often mounted externally, immediately adjacent to the impact area, and are thus subject to damage from collision debris.

SUMMARY

This Summary and Abstract are provided herein to introduce a selection of concepts in simplified form that are further described below in the Detailed Description. The Summary and Abstract are not intended to identify key features or essential features of the claimed subject matter, nor are they intended to be used as an aid in determining the scope of the claimed subject matter. The claimed subject matter is not limited to the implementations that solve any or all the disadvantages noted in the background.

One general aspect includes an impact sensor body having a body of material with a striking edge and surfaces extending rearwardly from the striking edge defining upper and lower surfaces and side surfaces extending between the upper and lower surfaces. A primary aperture extends through the body of material between the upper and lower surfaces, or between the side surfaces. The primary aperture is located on a centerline between the side surfaces and transverse to the striking edge, where a secondary aperture extends through the body of the material between the upper and lower surface, or between the side surfaces, the secondary aperture being on the centerline and spaced apart from the primary aperture to form a flexure member.

Another general aspect includes an impact sensor body having a body of material with a striking edge with surfaces extending rearwardly from the striking edge defining upper and lower surfaces and side surfaces extending between the upper and lower surfaces, where a plurality of apertures (e.g. a primary aperture and a secondary aperture) is configured within the body of material to form a flexure member orthogonal to a direction of motion to strike an object.

Implementations may include one or more of the following features. The impact sensor body is configured where a surface of the flexure member forms part of an inner surface of the primary aperture. The impact sensor body where the body of material is configured to create tensile stresses causing tensile strains on the surface of the flexure member that are parallel with the striking edge with impact on the striking edge. The impact sensor body where the surface of the flexure member is flat. The impact sensor body where the surface of the flexure member is curved. The impact sensor body of where the body of material is configured to create compressive stresses causing compressive strains on spaced apart surfaces of an inner surface of the primary aperture that are orthogonal to the striking edge with impact on the striking edge. The impact sensor body where each of the spaced apart surfaces are flat. The impact sensor body where each of the spaced apart surfaces are curved.

The impact sensor body can include strain sensors disposed on the inner surface of the primary aperture having tensile stresses causing tensile strains parallel with the striking edge and/or compressive stresses causing compressive strains orthogonal to the striking edge with impact on the striking edge. For example, the strain sensors include resistive strain gages or capacitive strain gages. A port of size opening can be provided with access to an inner surface of the primary aperture, the port being of size for signal wires of the strain sensors. The strain sensors are electrically connected to form a wheatstone bridge. The impact sensor body is typically configured such that the flexure member is orthogonal to a direction of motion to strike an object. In embodiments, the at least one pair of the upper and lower surfaces, or the side surfaces are tapered extend rearwardly from the striking edge.

DETAILED DESCRIPTION

The following detailed description is not to be taken in a limiting sense, but is made merely for the purpose of illustrating the general principles of the apparatus described herein.

Figure 1:
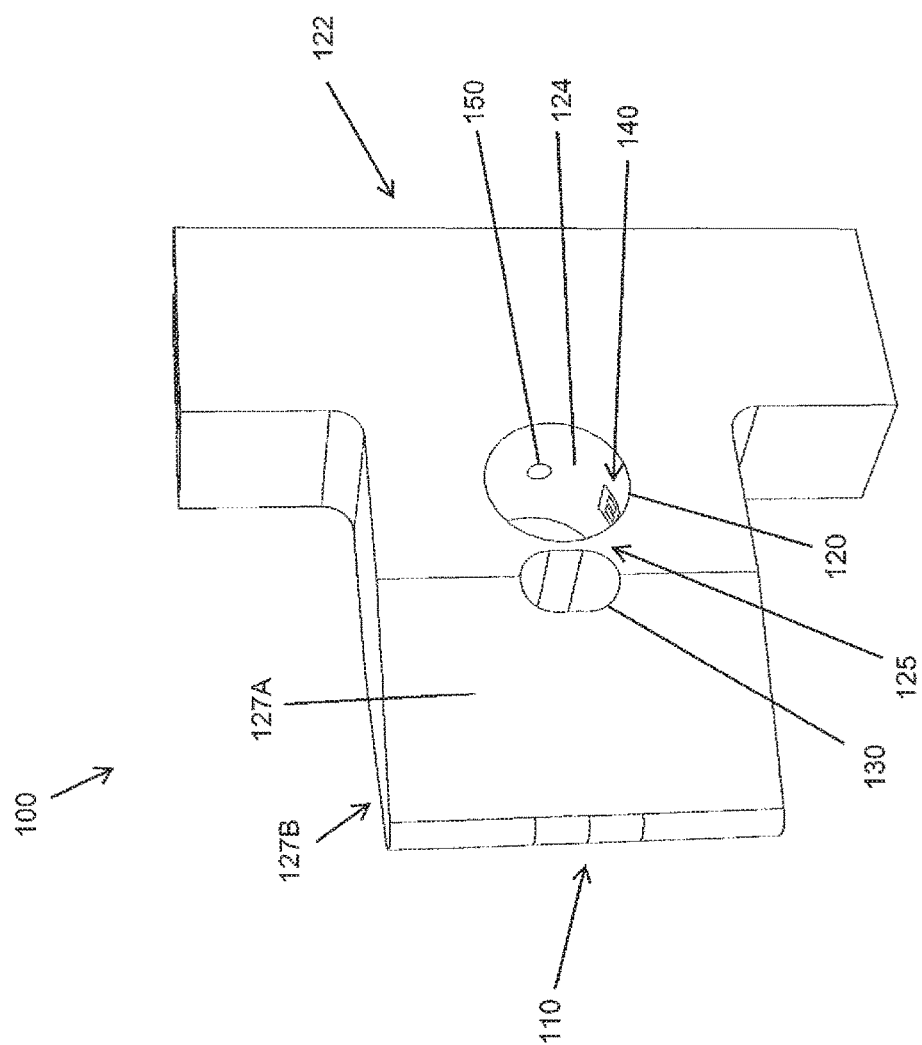
FIG. 1 is a perspective view of a sensor body.

This disclosure describes a reusable impact sensor with a high sensor output. FIG. 1 illustrates an embodiment of an impact sensor body 100 (i.e. Charpy sensor body) which includes a striking edge 110 to impact an object. Tapered surfaces extend rearwardly from striking edge 110 to form upper and lower surfaces. A secondary aperture 130 is disposed behind the striking edge 110 along the center of the impact force extending between surfaces 127A and 127B, herein referred to as upper and lower surfaces, respectively. A primary aperture 120 is disposed adjacent to the secondary aperture 130 along the center of percussion within the sensor body 100 of material. The primary aperture 120 and the secondary aperture 130 are narrowly placed together to form a flexure member 125 between them. Sensing elements 140 for measuring strain and their associated circuit wires (not shown) may be located within the interior of the primary aperture 120. The wires may connect the sensing elements 140 to external calibration equipment through port 150 extending through the sensor body 100 to a rear side 122 opposite the striking edge 110. Generally, the body of material 100 is configured such that the flexure member 125 is orthogonal to a direction of motion of the body when striking an object.

The primary aperture 120 may be a cylindrical hole placed approximately in the center of the sensor body 100 measured from the striking edge 110 to the rear side 122, preferably orthogonal to a center plane disposed on centerline 119 (extending from the striking edge 110 to the rear side 122) located between side surfaces 127A and 127B and parallel thereto. The secondary aperture 130 may be a smaller hole placed between the primary aperture 120 and the striking edge 110 to form the narrow flexure member 125, also preferably orthogonal to a center plane 1 disposed on centerline 119 located between side surfaces 127A and 127B and parallel thereto.

Figure 5:
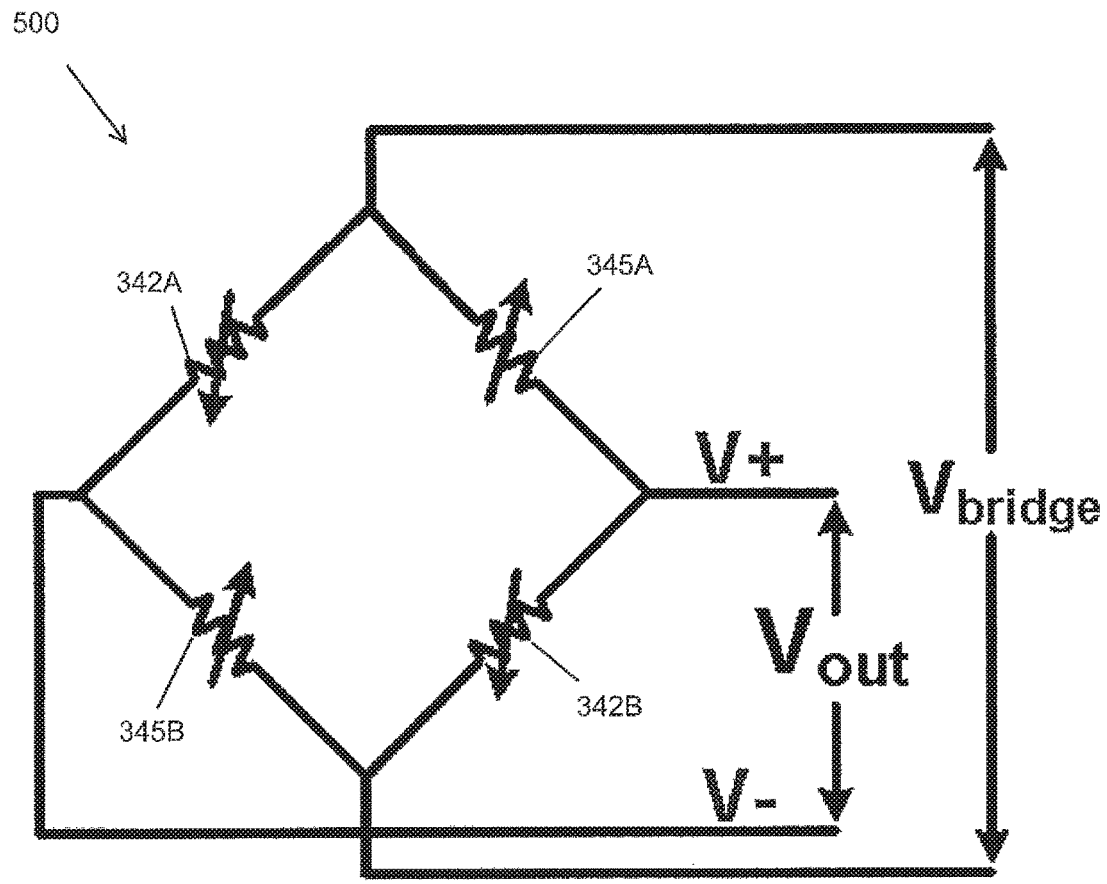
FIG. 5 is a schematic circuit of a Wheatstone bridge.

The sensing elements 140 may take any number of forms such as but not limited to strain gages (resistive or capacitive) used to measure the strain in portions of the sensor body 100 to which they are attached. The primary aperture 120 and flexure member 125 are formed to provide portions of the sensor body 100 that are in tension and compression with the added benefit that the sensing elements 140 are protected during testing. In the exemplary embodiment, deformation of the strain gages changes their electrical resistance which may be measured using a Wheatstone bridge 500 (FIG. 5).

Figure 2:
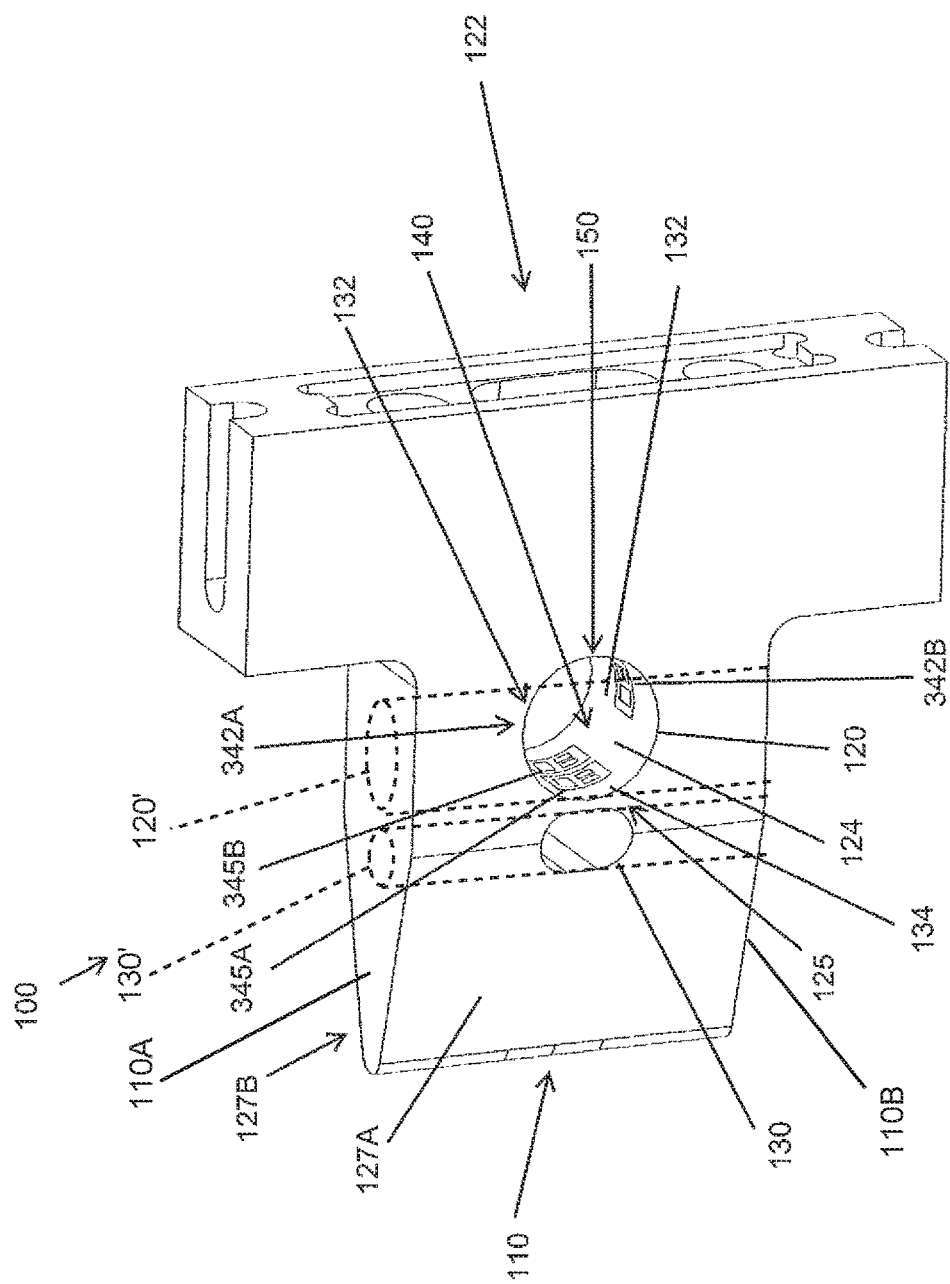
FIG. 2 is an alternative perspective view of the sensor body.
Figure 6:
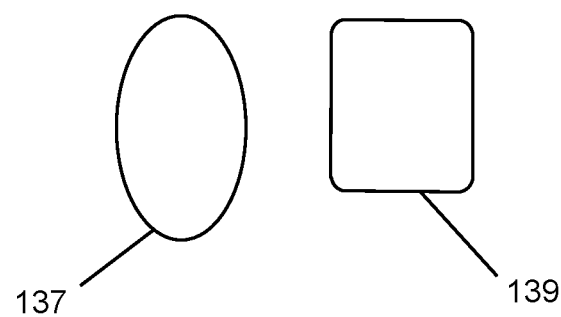
FIG. 6 is a schematic view of other aperture shapes.

FIG. 2 illustrates a rear perspective view of the sensor body 100 wherein the sensing elements 140 are configured so as to sense strain on regions of an inner surface 124 forming the primary aperture 120. When the sensor body 100 strikes a sample with the striking edge 110, the force is transmitted through the material of the sensor body 100, deforming portions of the inner surface 124. In particular, the impact force causes the primary aperture 120 to deform by shortening the primary aperture 120 along the centerline 119. The deformation of the primary aperture 120 causes focused compressive stress which causes compressive strains to occur on surfaces 132 of the primary aperture 120 generally transverse to the striking edge 110, and focused tensile stress which causes tensile strains to occur on surface 134 of the thinner material of the flexure member 125. Stated another way, the sensor body 100 is configured using the apertures 120, 130 to create tensile stresses causing tensile strains on the surface of the flexure member 125 that are parallel with the striking edge 110 with impact on the striking edge 110. Likewise the sensor body 100 is configured using the apertures 120, 130 to create compressive stresses causing compressive strains on spaced apart surfaces 132 of the inner surface 124 of the primary aperture 120 that are orthogonal to the striking edge 110 with impact on the striking edge 110. Stated yet another way, the apertures 120, 130 are provided to form the flexure member 125 so as to be orthogonal to a direction of motion of the striking edge 110. Defined in this manner, it should be noted that the apertures 120', 130' can extend through the sensor body 100 from side surfaces 110A and 110B to form the flexure member 125 in the same orientation in another embodiment. At this point it should be noted the shapes of apertures 120, 120', 130 and 130' can take any number of configurations. In the embodiment of FIGS. 1-4, primary aperture 120 is circular, while secondary aperture 130 is obround (i.e. racetrack configuration; however, this should not be considered limiting. FIG. 6 illustrates two other exemplary aperture configurations where shape 137 is an oval and 139 is rectangular, preferably with rounded corners. Apertures 120, 120', 130 and 130' can take any number of configurations the afore-mentioned shapes in any combination. In addition, if desired, one of the primary or secondary apertures can extend from surface 127A to 127B, while the other extends from side 110A to 110B. Hence, the portions of the inner surface 124 of the primary aperture 120 forming surfaces 132A, 132B and surface 134 can be flat or planer, and/or be slightly curved in any combination as desired.

Furthermore it should be noted that in the illustrative embodiment, the primary aperture 120 and secondary aperture 130 are disposed on portions of the upper and lower surfaces 127A, 127B where there exists a taper between the upper and lower surfaces 127A, 127B; however, this should not be considered limiting. If desired, the primary aperture 120 and/or the secondary aperture 130 can also be disposed through surface portions of the upper and lower surfaces that are parallel (similar to how side surfaces 110A and 110B are parallel to each other). Likewise, if desired, the side surfaces 110A, 110B can be tapered with respect to each other. Finally, one of the primary aperture and the secondary aperture can be located extending through tapered or parallel apertures, while the other also extends through tapered or parallel apertures. In short, the outer configuration of the upper and lower surfaces and the side surfaces with respect to forming the flexure 125 does not matter.

Figure 3:
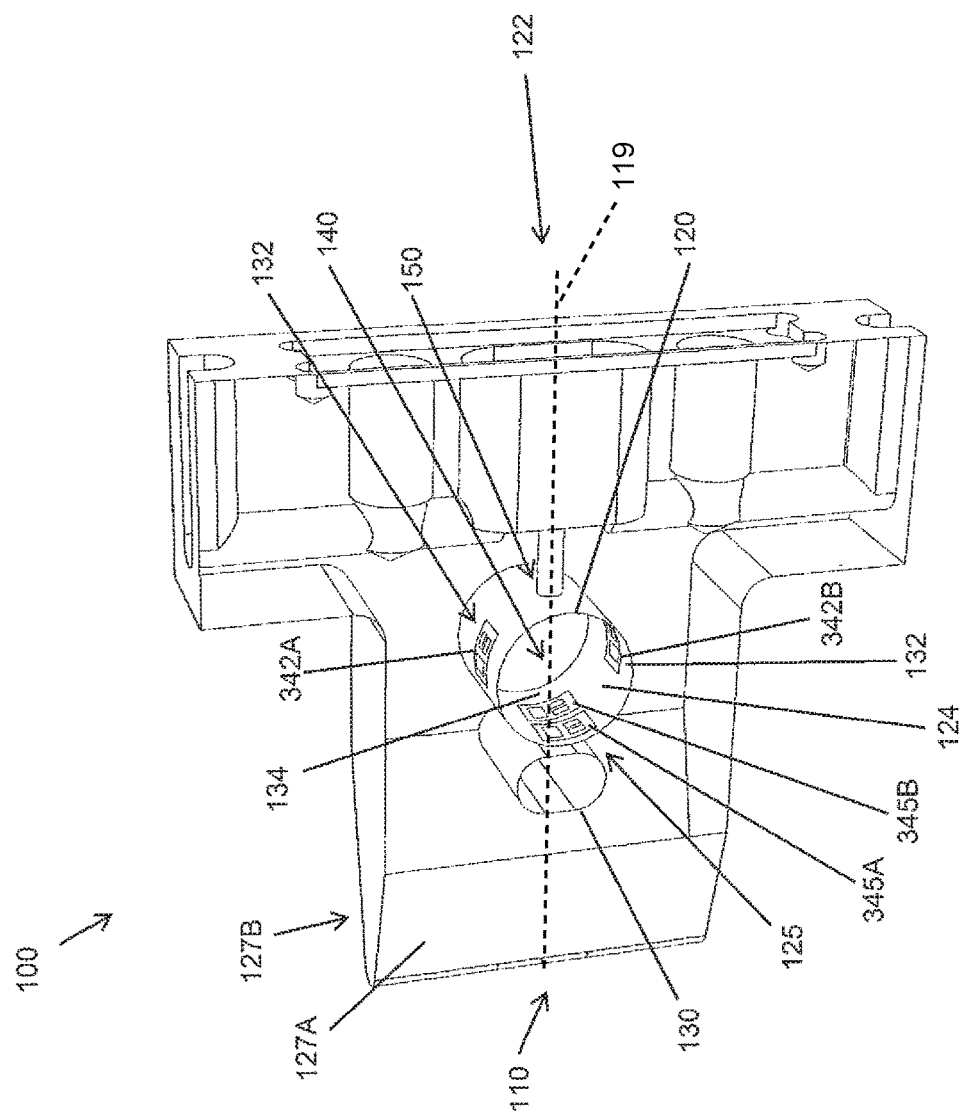
FIG. 3 is a schematic view of the sensor body.
Figure 4:
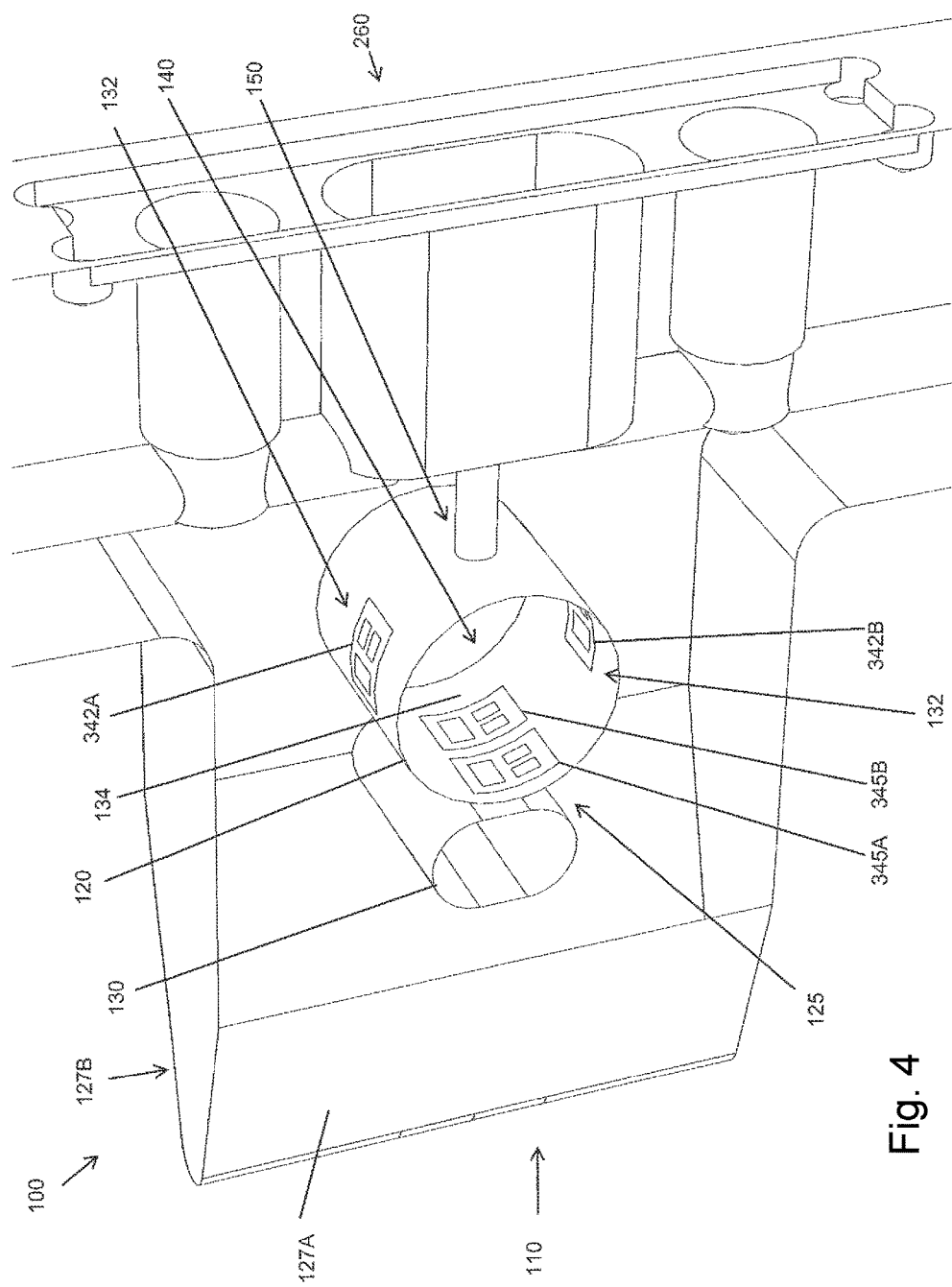
FIG. 4 is an enlarged schematic view of the sensor body.

FIGS. 3 and 4 are schematic illustrations of the sensor body 100. Generally, the sensor body is made from a single unitary body so that flexure 125 member is formed integral therewith. The schematic illustrations of FIGS. 3 and 4 illustrate various apertures and recesses within body 100 as having thin walls; however, it should be understood that solid material actually extends throughout the sensor body 100 between the thin walls of the various apertures and recesses. In the exemplary embodiment of FIGS. 3 and 4, sensing elements 140 on the inner surface 124 of the primary aperture 120, which include strain gages 342A, 342B on surfaces 132 and gages 345A, 345B on surface 134 of the flexure member 125 (see also FIG. 2). (If primary aperture 120 is circular or oval, the inner surface 124, surfaces 132 and surface 134 are slightly curved. Preferably, the strain gages 342A, 342B, 345A and 345B are disposed on the inner surface where surfaces 132 are tangentially orthogonal to striking edge 110 and where surface 134 is tangentially parallel to striking edge 110.) Wires from the sensing elements 140 may exit from the primary aperture 120 through the port 150 to the rear side 122. The primary aperture 120 and port 150 protect the sensing elements 140 and associated wires from damage due to debris from the collision event when the sensor body 100 strikes an object.

FIG. 5 illustrates a schematic circuit of a Wheatstone bridge 500 formed by strain gages 342A, B and 345A, B.

The impact sensor body 100 may be manufactured using subtractive methods using a plurality of materials. In one embodiment, the impact sensor body 100 may be made of extremely stiff material, with minimal mass located near the striking edge 110.

Although the present invention has been described with reference to preferred embodiments, workers skilled in the art will recognize that changes may be made in form and detail without departing from the spirit and scope of the invention.

What is claimed is:

1. An impact sensor body comprising
a body of material having a striking edge formed on a portion of an outer perimeter edge of the body with surfaces extending rearwardly from the striking edge defining upper and lower surfaces and side surfaces extending between the upper and lower surfaces, wherein a primary aperture extends through the body of material between the upper and lower surfaces, or between the side surfaces, at least a portion of the primary aperture being located on a centerline between the side surfaces, wherein a secondary aperture extends through the body of the material between the upper and lower surface, or between the side surfaces, at least a portion of the secondary aperture being on the centerline and spaced apart from the primary aperture to form a flexure member between the primary aperture and the secondary aperture, wherein the body of material is configured to create tensile stresses causing tensile strains on a surface of the flexure member that are parallel with the striking edge with impact on the striking edge.

2. The impact sensor body of claim 1 wherein the surface of the flexure member forms part of an inner surface of the primary aperture.

3. The impact sensor body of claim 2 wherein the primary aperture inner includes spaced apart surfaces that are flat.

4. The impact sensor body of claim 2 wherein the primary aperture inner includes spaced apart surfaces that are curved.

5. The impact sensor body of claim 1 wherein the body of material is configured to create compressive stresses causing compressive strains on spaced apart surfaces of an inner surface of the primary aperture that are orthogonal to the striking edge with impact on the striking edge.

6. The impact sensor body of claim 5 wherein each of the spaced apart surfaces are flat.

7. The impact sensor body of claim 5 wherein each of the spaced apart surfaces are curved.

8. The impact sensor body of claim 2 and comprising strain sensors disposed on the inner surface of the primary aperture having tensile stresses causing tensile strains parallel with the striking edge and/or compressive stresses causing compressive strains orthogonal to the striking edge with impact on the striking edge.

9. The impact sensor body of claim 8 wherein the strain sensors comprise resistive strain gages.

10. The impact sensor body of claim 8 wherein the strain sensors comprise capacitive strain gages.

11. The impact sensor body of claim 8 and comprising a port of size opening to the inner surface of the primary aperture, the port of size for signal wires of the strain sensors.

12. The impact sensor body of claim 8 wherein the strain sensors are electrically connected to form a Wheatstone bridge.

13. The impact sensor body of claim 1 wherein the body of material is configured such that the flexure member is orthogonal to a direction of motion to strike an object.

14. The impact sensor body of claim 1 wherein the upper and lower surfaces are tapered extending rearwardly from the striking edge, or the side surfaces are tapered extending rearwardly from the striking edge.

15. An impact sensor body includes a body of material having a striking edge along a portion of an outer perimeter edge of the body with surfaces extending rearwardly from the striking edge defining upper and lower surfaces and side surfaces extending between the upper and lower surfaces, wherein a plurality of apertures are configured within the body of material to form a flexure member between two apertures of the plurality of apertures that is orthogonal to a direction of motion to strike an object with the striking edge, wherein the body of material is configured to create compressive stresses causing compressive strains on spaced apart surfaces of an inner surface of one of the apertures of the plurality of apertures forming the flexure member that are orthogonal to the striking edge with impact on the striking edge.

16. The impact sensor body of claim 15 wherein at least one of the apertures of the plurality of apertures extends between the upper and lower surfaces.

17. The impact sensor body of claim 15 wherein at least one of the apertures of the plurality of apertures extends between the side surfaces.

18. The impact sensor body of claim 15 wherein the pair of upper and lower surfaces are tapered, or the side surfaces are tapered.

19. A body of material having a striking edge formed on a portion of an outer perimeter edge of the body with surfaces extending rearwardly from the striking edge defining upper and lower surfaces and side surfaces extending between the upper and lower surfaces, wherein a primary aperture extends through the body of material between the upper and lower surfaces, or between the side surfaces, wherein a secondary aperture extends through the body of the material between the upper and lower surface, or between the side surfaces, wherein the secondary aperture is spaced apart from the primary aperture to form a flexure member between the primary aperture and the secondary aperture that is parallel to the striking edge, wherein the body of material is configured to create tensile stresses causing tensile strains on a surface of the flexure member that are parallel with the striking edge with impact on the striking edge, and wherein the body of material is configured to create compressive stresses causing compressive strains on spaced apart surfaces of an inner surface of the primary aperture that are orthogonal to the striking edge with impact on the striking edge.

\* \* \* \* \*